United States Patent [19]

Yoshida et al.

[11] Patent Number: 5,023,351

[45] Date of Patent: Jun. 11, 1991

[54] α-(ω-CYANOALKANOYL-GAMMA BUTYROLACTONE AND METHOD FOR PRODUCING THE SAME

[75] Inventors: Hiroshi Yoshida; Noboru Kakeya; Masanori Kashiwagi, all of Ube, Japan

[73] Assignee: Ube Industries, Ltd., Ube, Japan

[21] Appl. No.: 529,897

[22] Filed: May 29, 1990

[30] Foreign Application Priority Data

Jun. 6, 1989 [JP] Japan .................................. 1-142102

[51] Int. Cl.$^5$ ............................................ C07D 307/33
[52] U.S. Cl. ...................................... 549/321; 549/322
[58] Field of Search ................................. 549/321, 322

[56] References Cited

U.S. PATENT DOCUMENTS

| | | | |
|---|---|---|---|
| 3,819,714 | 6/1974 | Bluestone et al. | 549/321 |
| 3,973,944 | 8/1976 | Erdmann et al. | 549/321 |
| 4,285,868 | 8/1981 | Heiba et al. | 549/321 |

FOREIGN PATENT DOCUMENTS 0348549 1/1990 European Pat. Off. .

*Primary Examiner*—Frederick E. Waddell
*Assistant Examiner*—Ba K. Trinh
*Attorney, Agent, or Firm*—Frishauf, Holtz, Goodman & Woodward

[57] ABSTRACT

Disclosed are α-(ω-Cyanoalkanoyl)-γ-butyrolactone represented by the formula:

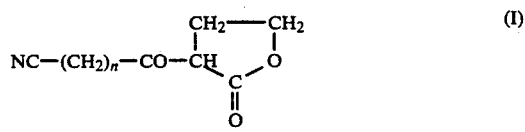

wherein n represents an integer of 7 to 11, and a method for producing the same, which comprises reacting ω-cyano fatty acid ester represented by the formula:

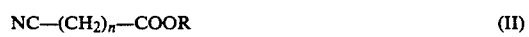

wherein R represents an alkyl group having 1 to 4 carbon atoms and n has the same meaning as in the above, with γ-butyrolactone in the presence of alkali metal alcoholate represented by the formula:

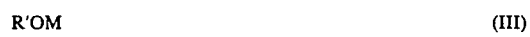

wherein R' represents an alkyl group having 1 to 4 carbon atoms and M represents an alkali metal.

6 Claims, No Drawings

α-(ω-CYANOALKANOYL)-γ-BUTYROLACTONE AND METHOD FOR PRODUCING THE SAME

BACKGROUND OF THE INVENTION

This invention relates to α-(ω-cyanoalkanoyl)-γ-butyrolactone, which is a novel intermediate lactone in the preparation of ω-hydroxy fatty acid, which is useful as a starting material and intermediate of various syntheses, particularly an important intermediate of macrocyclic lactone type perfumes in the field of perfume industry.

α-(ω-cyanoalkanoyl)-γ-butyrolactone which produced according to the present invention is a novel compound.

There have been known many methods for producing ω-hydroxy fatty acid which is an important intermediate of macrocyclic lactone type perfumes. Typical examples thereof are introduced in "Perfume Chemical Comprehensive 2", by Osamu Okuda, Hirokawa Shoten, p. 1211 and "Perfume Chemical Comprehensive 3", by Osamu Okuda, Hirokawa Shoten, p.p. 172-174 and 176-177.

The above methods include several drawbacks that these have many steps and are troublesome in handling, expensive agents or agents accompanied by dangers in handling are often required, and also the yield is poor.

Accordingly, these methods are not advantageous methods in industrial view.

SUMMARY OF THE INVENTION

An object of the present invention is to provide α-(ω-cyanoalkanoyl)-γ-butyrolactone, a novel compound as a starting material in the preparation of ω-hydroxy fatty acid, which can solve the above drawbacks in the prior art and a method for producing the same.

The present inventors found that α-(ω-cyanoalkanoyl)-65 -butyrolactone represented by the formula:

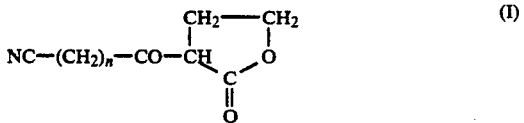

wherein n represents an integer of 7 to 11, can be obtained easily at high yield by reacting ω-cyano fatty acid ester represented by the formula:

$$NC-(CH_2)_n-COOR \quad (II)$$

wherein R represents an alkyl group having 1 to 4 carbon atoms and n has the same meaning as in the above, with γ-butyrolactone in the presence of alkali metal alcoholate represented by the formula:

$$R'OM \quad (III)$$

wherein R' represents an alkyl group having 1 to 4 carbon atoms and M represents an alkali metal, and accomplished the present invention.

DESCRIPTION OF THE PREFERRED EMBODIMENTS

α(ω-cyanoalkanoyl)-γ-butyrolactone of the formula (I) obtained by the present invention can be easily derived at high yield to ω-hydroxy fatty acid (V) which is an important intermediate of macrocyclic lactone type perfumes throughtthe steps shown below.

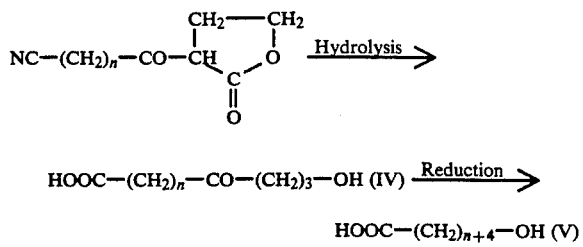

$$HOOC-(CH_2)_n-CO-(CH_2)_3-OH \quad (IV) \xrightarrow{Reduction}$$

$$HOOC-(CH_2)_{n+4}-OH \quad (V)$$

More specifically, α-(ω-cyanoalkanoyl)-γ-butyrolactone of the formula (I) can be converted to ω-hydroxy-(ω-3)-keto fatty acid of the formula (IV) by heating in an aqueous solution of alkali metal hydroxide or a water-soluble organic solvent/water mixture to hydrolyze the —CN group to —COOH group and hydrolyze and decarboxylate the lactone site to a —(CH$_2$)$_3$—OH group.

Then, the —CO— group of the formula (IV) is reduced to a —CH$_2$—group by ordinary procedures, Clemmensen reduction or Wolff-Kishner reduction to derive the compound (IV) to ω-hydroxy fatty acid (V).

Specific examples of α-(ω-cyanoalkanoyl)-γ-butyrolactone of the formula (I) may include, α-(8-cyanooctanoyl)-γ-butyrolactone, α-(9-cyanononanoyl)-γ-butyrolactone, α-(10-cyanodecanoyl)γ-butyrolactone, α-(11-cyanoundecanoyl)-γ-butyrolactone and α-(12-dodecanoyl)-γ-butyrolactone.

Specific examples of ω-cyano fatty acid ester of the formula (II) may include methyl 8-cyanooctanate, ethyl 8-cyanoctanate, propyl 8-cyanooctanate, butyl 8-cyanooctanate, methyl 9-cyanononanate, ethyl 9-cyanononanate, propyl 9-cyanononanate, butyl 9-cyanononanate, methyl 10-cyanodecanate, ethyl 10-cyanodecanate, propyl 10-cyanodecanate, butyl 10-cyanodecanate, methyl 11-cyanoundecanate, ethyl 11-cyanoundecanate, propyl 11-cyanoundecanate, butyl 11-cyanoundecanate, methyl 12-cyandodecanate, ethyl 12-cyanododecanate, propyl 12-cyanododecanate, butyl 12-cyanododecanate and the like.

The ω-cyano fatty acid ester of the formula (II) may be used in the range of 0.3 to 10 mole, preferably 0.5 to 5 mole per mole of γ-butyrolactone. In the instance where the employed amount is less than the lower limit, the yield will be lowered, while in the instance where the employed amount exceeds the upper limit, although no problem occurs in the yield, the recovery amount of unreacted ω-cyano fatty acid ester of the formula (II) will be increased to make the method disadvantageous in economical view. Both instances are thus not preferable.

Specific examples of alkali metal alcoholate of the formula (III) may include sodium methylate, sodium ethylate, sodium propylate, sodium butylate, potassium methylate, potassium ethylate, potassium propylate, potassium butylate and the like. The alkali metal alcoholate should advantageously be used under the state of an alcohol solution corresponding to the alcoholate in a viewpoint of operability.

The alkali metal alcoholate of the formula (III) may be used in the range of 0.5 to 2 mole, preferably 0.7 to 1.5 mole per mole of γ-butyrolactone. In the instance where the employed amount is less than the lower limit, the reaction does not proceed sufficiently, while in the instance where the employed amount exceeds the upper limit, side reactions will often occur. Both instances are thus not preferable.

In the method of the present invention, a reaction solvent may be used with no problem. As the reaction solvent, n-hexane, n-heptane, benzene, toluene, xylene, dioxane, dimethoxyethane, diethoxyethane, diglaim, etc. may be included. When such solvents are used, it is preferable to use a solvent having a boiling point higher than that of the alcohol produced in the reaction.

The reaction temperature is in the range of 50 to 150° C., preferably 80 to 120° C.

The reaction can be carried out under the condition of atmospheric pressure, but may be carried out under the reduced pressure to rapidly evaporate the alcohol which is used for accelerating the reaction, to the outside of system.

The reaction time, which is appropriately selected depending on the reaction temperature, kind of starting material charged and the like, may generally be around 1 to 5 hours.

The reaction may be carried out by either a batch system or a continuous system.

Isolation and purification of the reaction product can be effected according to a unit operation which is itself well known such as neutralization, extraction, concentration, recrystallization or the like.

By utilizing $\alpha$-($\omega$-cyanoalkanoyl)-$\gamma$-butyrolactone of the formula (I) novelly found by the present inventors, $\omega$-hydroxy fatty acid of the formula (V), which is an important intermediate of macrocyclic lactone type perfumes, can be obtained at high yield by simple operation from inexpensive and easy-available starting material through three steps significantly shortened as compared with the conventional methods. Furthermore, $\alpha$-($\omega$-cyanoalkanoyl)-$\gamma$-butyrolactone of the formula (I) is also widely useful as an intermediate lactone.

The present invention is described in more detail by referring to examples.

EXAMPLE 1

18.03 g (80.0 millimole) of methyl 11-cyanoundecanate, 3.44 g (40.0 millimole) of $\gamma$-butyrolactone and 7.72 g (40.0 millimole) of 28 wt.% of sodium methylate - methanol solution were charged into a frask and heated and stirred until the internal temperature became 105 to 110° C. while evaporating off the methanol out of the system over 2 hours. After the completion of the reaction, the system was cooled and made acidic by use of 43 ml of 1N-HCl, followed by extraction once from 100 ml of methylene chloride and two times from 20 ml of methylene chloride. After the methylene chloride solution was dried over magnesium sulfate, concentration was conducted to dryness to obtain pail brown oily product. The obtained oily product was purified with use of a silicagel column by using n-hexane/ethyl acetate (1:1, volume ratio) as a developer to obtain 7.93 g (28.4 millimole, yield: 71 %) of a white solid.

The results of analysis of the white solid are shown below.

(1) m.p. 57 to 59° C.
(2) elemental analysis (in terms of $C_{16}H_{25}NO_3$)

|  | C | H | N |
|---|---|---|---|
| Calculated (%) | 68.79 | 9.02 | 5.01 |
| Found (%) | 68.67 | 9.06 | 5.22 |

(3) IR (KBr,cm$^{-1}$): 2920, 2850, 2250, 1780, 1705
(4) MS (m/e, CI): 280 (M$^+$+1):
(5) 1H-NMR (CDCl$_3$, $\delta$(ppm)): 1.20~1.37 (10H, broad) 1.37~1.50 (2H, m), 1.62~1.69 (4H, m), 2.26~2.36 (3H, m), 2.56~2.64 (1H, m), 2.72~2.80 (1H, m), 2.91~3.00 (1H, m), 3.68~3.72 (1H, m), 4.29~4.41 (2H, m)

From the above respective analysis results, it was confirmed that the product was $\alpha$-(11-cyanoundecanoly)-$\gamma$-butyrolactone

EXAMPLES 2 to 5

With respect to 3.44 g (40.0 millimole) of $\gamma$-butyrolactone and 7.72 g (40.0 millimole) of 28 wt.% sodium methylate-methanol solution, the amounts shown in Table 1 of methyl 11-cyanoundecanate were charged in each example, and heated under stirring. When the evaporation of methanol from the reaction system started, the degree of reduced pressure of the reaction system was controlled to 610 to 630 Torr and then evaporation of methanol was continued until the internal temperature became 105 to 110 ° C. for 2 hours. After the completion of the reaction, the system was cooled and made acidic by use of 43 ml of 1N-HCl, followed by extraction once from 100 ml of methylene chloride and two times from 20 ml of methylene chloride. The product in the methylene chloride solution, $\alpha$-(11-cyanoundecanoly)-$\gamma$-butyrolactone and the unreacted methyl 11-cyanoundecanate were quantified with use of a gas chromatography according to the internal standard method. The results are shown in Table 1.

TABLE 1

| Example No. | Charged amount of methyl 11-cyano undecanate g (millimole) | $\alpha$-(11-cyanoundecanoly)-$\gamma$-butyrolactone Produced amount g (millimole) | Yield (%)*$^1$ | Amount of unreacted methyl 11-cyanoundecanate g (millimole) |
|---|---|---|---|---|
| 2 | 6.02 (26.7) | 5.50 (19.7) | 83 | 0.65 (2.9) |
| 3 | 9.01 (40.0) | 8.16 (29.2) | 73 | 2.19 (9.7) |
| 4 | 18.03 (80.0) | 9.39 (33.6) | 84 | 9.91 (44.0) |
| 5 | 36.05 (160) | 9.28 (33.2) | 83 | 27.7 (121) |

Note:
*$^1$The yield in Example 2 is the value based on methyl 11-cyanoundecanate having been reacted as a standard. In Examples 3 to 5, the yield is the value based on $\gamma$-butyrolactone charged as a standard.

EXAMPLE 6

9.01 g (40.0 millimole) of methyl 11-cyanoundecanate, 3.44 g (40.0 millimole) of $\gamma$-butyrolactone, 7.72 g (40.0 millimole) of 28 wt.% of sodium methylate - methanol solution and 10 ml of dioxane were charged and heated and stirred until the internal temperature became 105 to 107° C. while evaporating the methanol and dioxane to the outside of the system over 2 hours. After completion of the reaction, the system was cooled and made acidic by use of 43 ml of 1N-HCl, followed by extraction once from 100 ml of methylene chloride and two times from 20 ml of methylene chloride. The product in the methylene chloride solution, α-(11-cyanoundecanoly)-γ-butyrolactone and the unreacted methyl 11-cyanoundecanate were quantified in the same manner as in Example 3.

As a result of the analysis, the produced α-(11-cyanoundecanoly)-γ-butyrolactone was 8.38 g (30.0 millimole, Yield: 75 %) and the unreacted methyl 11-cyanoundecanate was 1.44 g (6.4 millimole).

EXAMPLE 7

19.15 g (80.0 millimole) of ethyl 11-cyanoundecanate, 3.44 g (40.0 millimole) of γ-butyrolactone and 18.15 g (40.0 millimole) of 15 wt.% of sodium ethylate - ethanol solution were charged into a frask and heated under stirring. When the evaporation of ethanol from the reaction system started, the degree of reduced pressure of the reaction system was controlled to 600 to 650 Torr and the evaporation of ethanol was continued until the internal temperature became 105 to 110 ° C. over 4 hours. After completion of the reaction, the system was cooled and made acidic by use of 43 ml of IN-HCl, followed by extraction once from 100 ml of methylene chloride and two times from 20 ml of methylene chloride. The product in the methylene chloride solution, α-(11-cyanoundecanoly)-γ-butyrolactone and the unreacted ethyl 11-cyanoundecanate were quantified with use of a gas chromatography according to the internal standard method. As a result, the produced α-(11-cyanoundecanoly)-γ-butyrolactone was 8.83 g (31.6 millimole, Yield: 79 %) and the unreacted ethyl 11-cyanoundecanate was 10.77 g (45.0 millimole).

REFERENCE EXAMPLE 1

Example of production of 15-hydroxy-12-ketopentadecanoic acid 0.279 g (1.00 millimole) of α-(11-cyanoundecanoyl)-γ-butyrolactone, 0.68 g (10.3 millimole) of 85 % potassium hydroxide and 5.66 g of water were charged and heated under reflux over 10 hours. After completion of the reaction, the system was cooled and made acidic by use of 5 ml of 4N-HCl, followed by extraction once from 70 ml of methylene chloride and two times from 20 ml of the same. After the methylene chloride solution was dried over sodium sulfate, concentration was conducted to dryness to obtain white solid. The obtained white solid was purified with use of a silicagel column by using n-hexane/ethyl acetate (1:1, volume ratio) as a developer to obtain 0.254 g (0.933 millimole, yield: 93 %) of a white solid.

The results of analysis of the white solid are shown below.

(1) m.p. 74° to 76 ° C.
(2) elemental analysis (in terms of $C_{15}H_{28}O_4$)

|  | C | H |
| --- | --- | --- |
| Calculated (%) | 66.14 | 10.36 |
| Found (%) | 66.16 | 10.47 |

(3) IR (KBr,cm$^{-1}$): 3250, 2920, 2850, 1700
(4) MS (m/e, CI): 255 (M$^+$ −17)
(5) 1H-NMR (CDCl$_3$, δ(ppm)): 1 18∼1.38 (12H, broad): 1.56∼1.65 (4H, m), 1.78∼1.89 (2H, broad), 2.33∼2.36 (4H, m), 2.44∼2.57 (2H, broad), 3.60∼3.70 (2H, broad)

From the above respective analysis results, it was confirmed that the product was 15-hydroxy-12-ketopentadecanoic acid.

REFERENCE EXAMPLE 2

Example of proudction of 15-hydroxy-pentadecanoic acid:

1.00 g (3.68 millimole) of 15-hydroxy-12-ketopentadecanoic acid, 0.73 g (11.0 millimole) of 85 wt.% potassium hydroxide, 0.50 g (8.5 millimole) of 85 % hydrated hydrazine and 5 ml of diethylene glycol were charged into a frask and heated under reflux over 1.5 hours. Subsequently, while evaporating the produced light boiling components such as water to the outside of the system, the internal temperature was elevated to 195 to 205° C., and the heating under reflux was continued at the same temperature range over 2 hours. After completion of the reaction, the solution was cooled, diluted by addition of 5 ml of water and added with 3 ml of 6N-HCl, followed by collection of the precipitated pail brown solid by filtration. The solid was recrystallized from benzene to obtain 0.81 g (3.14 millimole, Yield: 85 %) of a white crystl.

The results of analysis of the white solid are shown below.

(1) m.p. 83 to 85° C.
(2) elemental analysis (in terms of $C_{15}H_{30}O_3$)

|  | C | H |
| --- | --- | --- |
| Calculated (%) | 69.72 | 11.70 |
| Found (%) | 69.57 | 11.90 |

(3),(4) and (5)
The analysis values of IR, MS and 1-H-NMR were the same as those of a standard product.

From the above respective analysis values, it was confirmed that the product was 15-hydroxypentadecanoic acid.

We claim:
1. A α-(ω-cyanoalkanoyl)-γ-butyrolactone represented by the formula:

$$NC-(CH_2)_n-CO-CH \underset{\underset{O}{\overset{\|}{C}}}{\overset{\overset{CH_2-CH_2}{|\quad\quad|}}{}} O \quad\quad (I)$$

wherein n represents an integer of 7 to 11.
2. The α-(ω-cyanoalkanoyl)-γ-butyrolactone according to claim 1 which is α-(8-cyanooctanoyl)-γ-butyrolactone.
3. The α-(ω-cyanoalkanoyl)-65 -butyrolactone according to claim 1 which is α-(9-cyanononanoyl)-γ-butyrolactone.
4. The α-(ω-cyanoalkanoyl)-γ-butyrolactone according to claim 1 which is α-(10-cyanodecanoyl)-γ-butyrolactone.
5. The α-(ω-cyanoalkanoyl)-γ-butyrolactone according to claim 1 which is α-(11-cyanoundecanoyl)-γ-butyrolactone.
6. The α-(ω-cyanoalkanoyl)-γ-butyrolactone according to claim 1 which is α-(12-dodecanoyl)-γ-butyrolactone.

* * * * *